(12) United States Patent
Kirakosyan

(10) Patent No.: US 10,111,827 B2
(45) Date of Patent: Oct. 30, 2018

(54) HAIR LOSS PREVENTION AND RESTORATION SOLUTION

(71) Applicant: Ruzanna Kirakosyan, Glendale, CA (US)

(72) Inventor: Ruzanna Kirakosyan, Glendale, CA (US)

(73) Assignee: Blooming Rose Cosmetics, Inc., Glendale, CA (US)

( * ) Notice: Subject to any disclaimer, the term of this patent is extended or adjusted under 35 U.S.C. 154(b) by 106 days.

(21) Appl. No.: 15/250,246

(22) Filed: Aug. 29, 2016

(65) Prior Publication Data

US 2016/0367473 A1    Dec. 22, 2016

Related U.S. Application Data

(63) Continuation-in-part of application No. 14/320,176, filed on Jun. 30, 2014, now Pat. No. 9,427,394.

(51) Int. Cl.

| | |
|---|---|
| *A61K 36/00* | (2006.01) |
| *A61K 8/97* | (2017.01) |
| *A61K 8/73* | (2006.01) |
| *A61K 8/34* | (2006.01) |
| *A61K 8/92* | (2006.01) |
| *A61Q 7/00* | (2006.01) |
| *A61K 8/86* | (2006.01) |
| *A61K 8/49* | (2006.01) |
| *A61K 8/37* | (2006.01) |
| *A61K 8/39* | (2006.01) |
| *A61K 8/99* | (2017.01) |
| *A61K 8/65* | (2006.01) |

(52) U.S. Cl.
CPC ............... *A61K 8/97* (2013.01); *A61K 8/342* (2013.01); *A61K 8/345* (2013.01); *A61K 8/37* (2013.01); *A61K 8/39* (2013.01); *A61K 8/49* (2013.01); *A61K 8/65* (2013.01); *A61K 8/731* (2013.01); *A61K 8/86* (2013.01); *A61K 8/922* (2013.01); *A61K 8/99* (2013.01); *A61Q 7/00* (2013.01); *A61K 2800/5922* (2013.01)

(58) Field of Classification Search
CPC ..................................................... A61K 36/00
See application file for complete search history.

(56) References Cited

U.S. PATENT DOCUMENTS

| | | | | |
|---|---|---|---|---|
| 4,820,512 A | * | 4/1989 | Grollier | ............... A61K 8/4953 514/256 |
| 5,407,675 A | * | 4/1995 | Etemad-Moghadam | ................... A61K 8/922 424/401 |

\* cited by examiner

*Primary Examiner* — Qiuwen Mi
(74) *Attorney, Agent, or Firm* — Adli Law Group P.C.; Chen Huang

(57) ABSTRACT

The embodied invention generally pertains to compositions, and the methods of making and using said compositions for promoting hair growth, slowing hair loss, and for preventing or minimizing hair loss that are effective and able to treat multiple aspects of the problem in one product and additionally is comprised of natural oils and minerals which greatly reduce the toxicities and side effect issues associated with present products. The compositions or formulations of the present invention relate to a hair loss solution that solves the problems associated with the loss, and damage of hair by working from the root to the surface of the scalp and to the hair shaft by treating a plurality of the causes and/or triggers associated with hair loss, or the prevention of hair re-growth.

8 Claims, 3 Drawing Sheets

HAIR LOSS PREVENTION AND RESTORATION SOLUTION

CROSS-REFERENCE TO RELATED PATENT APPLICATIONS

The present application is a Continuation-in-Part Application to U.S. Utility patent application Ser. No. 14/320,176, filed Jun. 30, 2014, entitled "HAIR LOSS PREVENTION AND RESTORATION SOLUTION", the contents of which are incorporated by reference herein in its entirety and which is a basis for a claim of priority.

BACKGROUND OF THE INVENTION

There are many products on the market claiming to provide a solution to hair loss, however these products generally only treat one or two aspects of the problem or mask the problem altogether. There are multiple reasons for hair loss and damaged hair.

Hair loss affects both men and women. Often hair loss is caused by an imbalance of the hair growth cycle, DHT (dihydrotestosterone) formation, environmental and many more conditions. Hair loss or alopecia may also be caused by a variety of factors including heredity, hormonal deficiencies or imbalances, diet, stress, illnesses, chemotherapy or aging. The desire to maintain or regain head hair has led to continuing efforts throughout history to discover compositions and methods for stimulating hair growth and for preventing or minimizing hair loss.

For many years, the pharmaceutical industry, the nutraceutical industry, and the cosmetic industry have been researching and developing compositions in attempts to cure or prevent hair loss or promote hair growth.

There are surgical and non-surgical solutions to address the problem of hair loss. Non-surgical options for treating hair loss include a variety of pharmaceutical and nutraceutical topical and/or oral treatments that promote hair regrowth and/or prevent further hair loss. For example, topical minoxidil, commonly known as ROGAINE, causes hair growth when applied to the scalp and slows the rate of hair loss in some individuals by stimulating hair follicles. Finasteride, commonly known as PROPECIA is a drug that is taken orally to treat androgenic alopecia by blocking the formation of DHT. The problem with treating hair loss with pharmaceutical drugs is the potential side effects of such drugs. Minoxidil may cause low blood pressure, increase in heart rate, weight gain due to water retention, and the scalp may become inflamed. Finasteride may cause genital deformities in male infants, impotence, decreased libido, hives or rash, and swelling.

Thus, in spite of the advancements in the prior art, there is a need in the art for compositions for promoting hair growth, slowing hair loss, and for preventing or minimizing hair loss that are effective and able to treat multiple aspects of the problem in one product and additionally is comprised of natural oils and minerals which greatly reduce the toxicities and side effect issues of present products, and for methods of making and using such compositions.

SUMMARY OF THE INVENTION

The embodiments of the present invention generally relate to hair loss prevention and restoration products and more specifically to specific formulations used to improve user outcomes in regards to hair loss and prevention, by treating a plurality of the causes associated with hair loss in a single formulation.

Additional embodiments include compositions for promoting hair growth, slowing hair loss, and for preventing or minimizing hair loss that are effective and able to treat multiple aspects of the hair loss problem in one product and additionally is comprised of natural oils and minerals which greatly reduce the toxicities and side effect issues of present products, and for methods of making and using such compositions.

Embodiments of the present invention comprise of formulations of different oils and/or plant extracts that when formulated together, are able to reconstruct and rejuvenate the hair follicle and scalp in order to restore hair growth and prevent further hair loss.

In one embodiment of the present invention, a formulation for use in the treatment of hair loss is disclosed. The formulation comprises: Rose water, *Eucalyptus* oil, Castor oil, Thyme oil, Rosemary Oil, German Chamomile Oil, Carrot Oil, Cederwood oil, Grape seed oil, *Arnica* oil, and Pseudocollagen. Further embodiments may also include at least one of the oils selected from coconut oil, sweet almond oil, olive oil, lavender oil, jojoba oil, aloe vera oil, tea tree oil or coconut oil. Still further embodiments may also include at least one of the ingredients selected from Vegetable glycerin, Shea Butter, Sage oil, Polyglyceryl Oleate, or PEG-7-Glyceryl Cocoate.

An additional embodiment includes a formulation including a total volume percent range for each ingredient including; 25% to 30% Rose water, 5% to 10% *Eucalyptus* oil, 5% to 8% Castor oil, 5% to 8% Thyme oil, 4% to 6% Rosemary Oil, 3% to 5% German Chamomile Oil, 3% to 5% Carrot Oil, 2% to 4% Coconut Oil, 2% to 4% Sweet Almond Oil, 1% to 3% Cederwood Oil, 1% to 3% Olive Oil, 1% to 3% Grape seed Oil, 1% to 3% Lavender Oil, 0.5% to 2.5% *Arnica* Oil, 0.5% to 2.5% Jojoba Oil, 0.5% to 2.0% *Aloe Vera* Oil, 0.5% to 2.0% Tea Tree Oil, 0.5% to 2.0% Pseudocollagen, 0.5% to 2.0% Vegetable glycerin, 0.5% to 2.0% Shea Butter, 0.1% to 0.6% Sage Oil, 8% to 12% Polyglyceryl Oleate, and 2% to 4% PEG-7-Glyceryl Cocoate.

A further additional embodiment includes a formulation with a total volume percentage for each ingredient including; 28.8% Rose water, 7.4% *Eucalyptus* Oil, 6.4% Castor Oil, 6.4% Thyme Oil, 5.3% Rosemary Oil, 4.3% German Chamomile Oil, 4.3% Carrot Oil, 3.2% Coconut Oil, 3.2% Sweet Almond Oil, 2.1% Cederwood Oil, 2.1% Olive Oil, 2.1% Grape seed Oil, 2.1% Lavender Oil, 1.6% *Arnica* Oil, 1.6% Jojoba Oil, 1.1% *Aloe Vera* Oil, 1.1% Tea Tree Oil, 1.1% Pseudocollagen, 1.1% Vegetable glycerin, 1.1% Shea Butter, 0.3% Sage Oil, 10.6% Polyglyceryl Oleate, and 2.7% PEG-7-Glyceryl Cocoate.

In yet another embodiment of the present disclosure, a formulation for use in the treatment of hair loss is disclosed. The formulation comprises: *Rosa Centifolia* Flower Water, Polyglyceryl-6 Distearate, Polyglyceryl-3 Diisostearate, *Thymus Vulgaris* (Thyme) Oil, *Eucalyptus Globulus* Leaf Oil, *Ocimum Basilicum* Hairy Root Culture Extract, *Helianthus Annuus* (Sunflower) Seed Oil, *Ricinus Communis* (Castor) Seed Oil, Jojoba Esters, *Arnica Montana*, Cetyl Alcohol, Glyceryl Stearate, *Cocos Nucifera* (Coconut) Oil, Ceteth-20, Steareth-20, Glycerin, *Acacia Decurrens* Flower Wax, *Helianthus Annuus* (Sunflower) Seed Wax, Polyglycerin-3, *Pisum Sativum* (Pea) Sprout Extract (Pea) Sprout Extract, Biotin, *Daucus Carota Sativa* (Carrot) Seed Oil, *Simmondsia Chinensis* (Jojoba) Seed Oil, *Butyrospermum Parkii* (Shea Butter), *Olea Europaea* (Olive) Oil, Algae Extract, Butylene Glycol, *Prunus Amygdaius Dulcis* (Sweet Almond) Oil, *Lavandula Angustifolia* (Lavender) Oil, *Melaleuca Alternifolia* (Tea Tree) Leaf Oil, Xanthan Gum, *Vitis Vinifera* (Grape) Seed Oil, *Juniperus Mexicana* Wood Oil, *Salvia Officinalis* (Sage) Oil, German Blue (*Matricaria Chamomilla*) Oil, Phenethyl Alcohol, Glycerine, *Citrus Reticulata* Fruit Extract, *Citrus Aurantium Amara* Fruit Extract, *Citrus Sinensis* Peel Extract, Ascorbic acid, Citric acid, Lactic acid.

A further additional embodiment includes a formulation with a total volume percentage for each ingredient including: 45% Rose Water, 4.80% *Eucalyptus* oil, 3% Castor Oil, 5% Thyme Oil, 0.14% Blue Chamomile Oil, 1.50% Carrot Seed Oil, 1% Coconut Oil, 1% Almond Oil, 0.50% cederwood, 1% Olive oil, 0.50% grape seed oil, 1% Lavender oil, 2% *Arnica* oil, 1% jojoba oil, 0.50% Tea tree, 1% Pseudocollogen, 2.50% Glycerin, 1.39% Shea Butter, 0.17% Sage oil, 2% AnaGain®, 2% RootBio TEC HO, 0.50% Biotin, 1% Sharon BioMix Free 1, 5% Tefose® HC, 6% Plurol® sterarique WL1009, 5% Plurol® Diisoctearique CG and 5% Acticire®, 0.50% Keltrol® CG.

Additional methods include methods of using the embodied formulations as described above to help prevent treat and restore hair regrowth and general scalp and hair health.

Yet further embodiments include methods for formulating the formulations as described above.

DETAILED DESCRIPTION OF THE PREFERRED EMBODIMENT(S)

Figure 1:
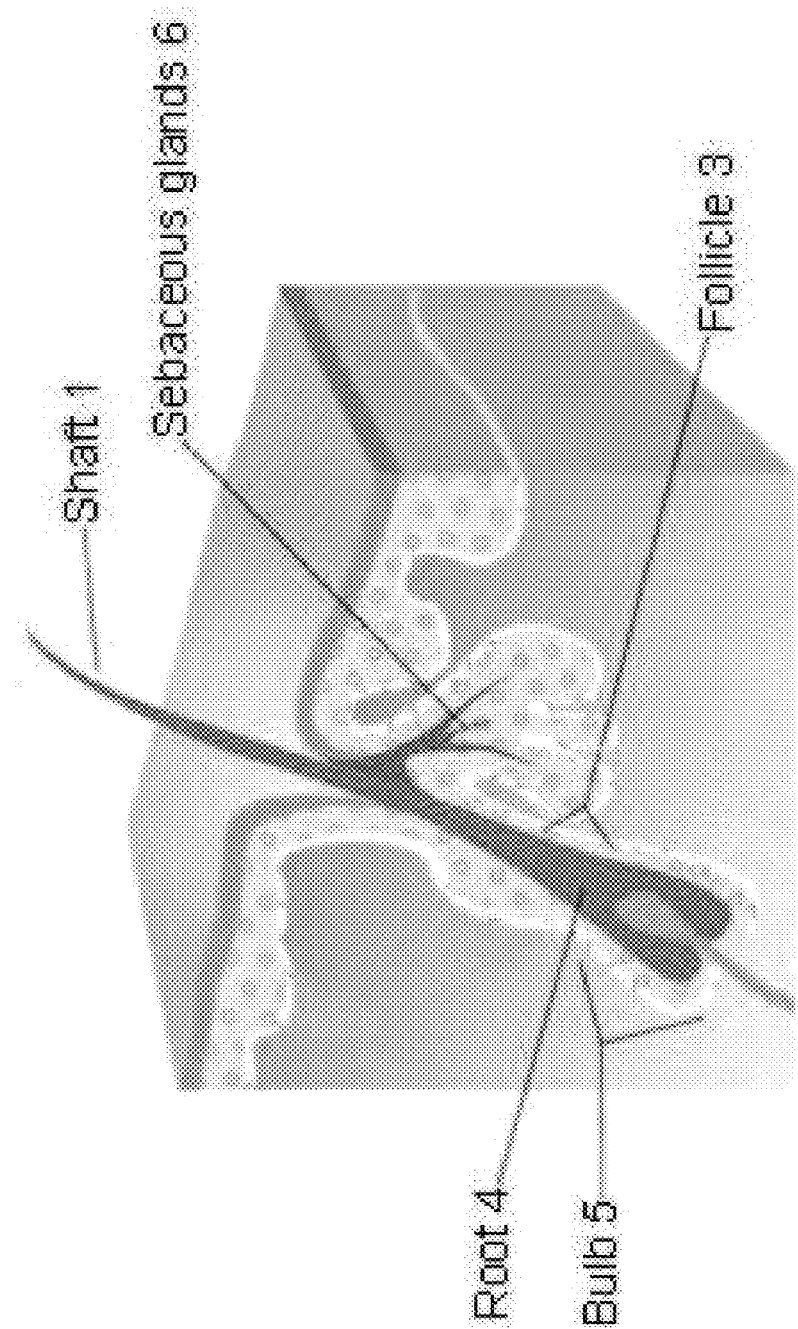
FIG. 1 demonstrates an illustration of a hair shaft in relation to the scalp.

FIG. 1 demonstrates a reference illustration of the anatomical components associated with hair and the scalp. The embodiments of the present invention relate to a hair loss solution that solves the problems associated with the loss, and damage of hair by working from the root 4 to the surface of the scalp 2 and to the hair shaft 1. Although there are many products that claim to work from the root 4 to the surface of the scalp 2 and the hair shaft 1, these products generally only treat one or two of the reasons or triggers that cause the underlying event or even worse they may mask these reasons or triggers leading to hair loss altogether.

As used herein, the term "hair loss" refers to loss of hair from the scalp or thinning of hair. The term "prevention of hair loss" refers to prevention and inhibition of the hair loss. And, the term "enhancement of hair growth" refers to enhancement of growth of new hair or healthy growth of existing hair.

Hair growth is affected by various factors including environmental factors such as temperature or sunlight, nutritional status of individuals and presence/absence of diseases, hormones, childbirth, exposure to radiation or various drugs, and so forth. The main causes of hair loss can be largely divided into internal physiological factors and external environmental factors. The internal physiological factors include, for example, increased activity of 5-alpha reductase which increases sebum secretion (from the sebaceous glands 6) by converting testosterone, an androgen, into dihydrotestosterone (DHT). The external environmental factors include, for example, malnutrition of the hair bulb 5 owing to insufficient blood circulation caused by constriction of blood vessels, dryness of the scalp 2, or the like. Accordingly, in order to prevent hair loss and enhance hair growth, it is necessary to nourish the hair bulb 5 by dilating blood vessels, supply substances that serve the same function as the constituents of hair directly to the hair bulb 5, remove excess sebum around the hair bulb 5 using a cleanser or an anti-sebum agent, or prevent dryness of the scalp using a moisturizer.

Because there are multiple triggers and reasons for hair loss and damaged hair as described above, the embodiments of the present invention are formulated to treat and minimize the problems that a person would have with their scalp 2 and hair 1 by addressing a broad range of hair loss triggers and reasons in a single formulation. The embodied product works with the scalp 2 and hair 1 to balance the pH to normal. Furthermore, the embodied formulation stabilizes the past, present and the future of the hair. In its first stage, an embodied formulation detoxifies the hair follicle 3 from all impurities from past products or internal impurities and stops the hair loss. In its second stage, the embodied formulations create better conditions for the hair 1 to grow by nourishing and strengthening the hair follicle 3. At the third stage, the formulation exhilarates hair re-growth. And at its fourth stage the formulation nourishes the hair from the root 4 to the tip of the hair 1. By nourishing the hair follicle 3 the hair shaft 1 is additionally nourished. The end result is beautiful and healthy looking hair that is healthy from the inside out. Users' notice the difference in the hair and that the hair has more body and shine. The combination of ingredients in the embodied formulations work together to produce great results for users experiencing hair loss and/or thinning and generally damaged hair.

The embodied formulations are generally comprised of all-natural products. The embodied formulations comprise of different oils and plant extracts and are formulated to reconstruct and rejuvenate the hair follicle in order to restore the hair. The embodied formulations help to stop the hair loss and rejuvenate the hair by restoring and nourishing the hair follicle.

Additionally, the embodied formulations may help with hair loss caused by illnesses, stress or environmental and chemical causes. The embodied formulations work by penetrating into the hair follicle, and detoxifying, nourishing and restoring the hair follicle to a more healthy form. This detoxification, nourishment and restoration of the hair follicle may be evident to a user after a single use, wherein the hair appears healthier, shinier, and more full of body and movement. Over time the user will notice that the hair becomes fuller and thicker. Unlike many products in the prior art the embodied formulations treat the root of the problem and does not mask the shortcomings by treating only the symptoms of unhealthy hair causing hair loss.

For best results using the embodied formulations the user first washes their hair and scalp thoroughly. The hair is towel dried and the formulation is applied to the hair and scalp by massaging the formulation on to the scalp. The formulation is then left on the scalp and in the hair for 20-30 minutes before it is rinsed out. In an optimized process for restoring hair and preventing hair loss the embodied formulations are applied as described above about 4 times a week for the first month and then tapered to 2 times a week thereafter. The more concentrated efforts at the beginning of the process help jumpstart the recovery of the hair follicle.

The studies with the formulations embodied showed a noticeable decrease in hair loss after 3-4 applications of the embodied formulations. Additionally, the hair was noticeably starting to re-grow after 1-3 months of use.

Studies were conducted on people with different issues associated with the hair and scalp. Some of the study participants had massive hair loss due to stress and/or medication, others from thyroid or other health related issues.

The people who had hair loss caused by stress, environment and medication had faster results. However, people with hair loss caused by thyroid and other health issues still showed positive results but more treatments were generally necessary before signs of improvement were observable.

Hair loss caused by secondary health issues showed faster results in improving the conditions of the scalp and hair. However, hair loss caused by primary health conditions were observed to take longer depending on the nature of the illness. In most people with secondary health issues, hair loss was noticeably decreased in 2-4 weeks. However, a person with primary health issues took about 6 to 12 weeks to notice the prevention of hair loss and the change in the texture of the hair, the time range was highly dependent what type of illness was associated with the primary health issue.

Any illness can and does effect the health of the rest of the body and its ability to properly nourish the skin and the hair internally. The embodied formulations maintain the nourishment of the skin and hair externally. The embodied formulations of the present invention help fill in the nutritional gaps that may be caused by the illness or malnourishment of the scalp and hair. Thereby, making the hair follicle strong enough to continuously maintain a healthy structure.

A list including the detailed information of the contemplated ingredients in the embodied formulations include:

Rose water. Rose water is known to have anti-inflammatory properties and to soothe irritated skin, it is also a great source of antioxidants which help to strengthen skin cells and regenerate skin tissue. Additionally, Rose water is known to stimulate the circulation of tiny blood vessels underneath the skin. Furthermore, Rose water assists in maintaining the skins pH balance, calms dermatitis and eczema. Rose water is known to hydrate and revitalize the skin while healing scars, cuts, and wounds that may be caused by various natural factors such as accidents, as well as from chemical damage to the scalp. Additionally, Rose water helps to hydrate and condition the hair shaft and helps make the hair shaft strong and flexible in order to help resist hair breakage.

Castor oil. Castor oil comprises vital components including nutrients, proteins, minerals and vitamin E which are all required for healthy hair. Castor oil is also rich in antibacterial and anti-fungal properties and has many fatty acids including ricindeic acid. Ricindeic acid helps to protect the hair and stimulates circulation of nutrient rich blood to the scalp. Furthermore, the full range of amino acids and omega-6 fatty acids found in castor oil help prevent split ends and hair breakage. Castor oil has the ability to penetrate deep in to the scalp and to smooth out rough hair and cuticles.

Thyme oil. Thyme oil is beneficial for scalp health and hair re-growth, the oil is powerfully concentrated and contains thymol, which is known to have antiseptic properties. Thyme oil provides benefit for cleansing and renewing the hair follicle. Thyme oil further contains pro-vitamin A, vitamin C and Keratin which are known to improve hair health.

Rosemary oil. Rosemary oil is one of the premier hair growth enhancing essential oils, which stimulate healthy hair growth. It is successfully used in *Alopecia areata* (hair-loss) treatment. Rosemary oils slow down premature hair loss and graying of hair. Rosemary oil is also beneficial for treating flaky scalps. Rosemary has the ability to strengthen the scalp and is beneficial in efforts to eliminate eczema, dermatitis and oily scalp.

German Chamomile Oil. German Chamomile oil is known to help calm eczema, rashes, wounds, dermatitis, dry and itchy skin. The oil is known to have anti-inflammatory and anti-infectious properties and also helps to calm allergic reactions to chemicals. The oil helps to regenerate skin tissue and may revitalize hair by straightening its root.

Coconut oil. Coconut oil is comprised of natural antioxidants and nutrients which when applied to hair help improve its softness and luster. The oil is rich in vitamin E, vitamin K and iron and effectively eliminates dandruff while boosting hair growth. Coconut oil effectively improves scalp circulation and boosts nutrient and oxygen delivery to hair. The fatty acids found within coconut oil bind to the protein in hair and protect both the roots and shaft of the hair from breakage. Specifically, Lauric acid, found in coconut oil improves hair health. Coconut oil serves two main functions when added to the embodied hair healing and protection embodiments. First, coconut oils hydrophobic properties allow it to inhibit the penetration of water from the surrounding air and environment. And second, coconut oil is able to bind to the natural protein structure of the hair, which helps hair retain it natural moisture content and reinforces the hair fiber thus, making it stronger.

Sweet almond oil. Sweet almond oil is a rich source of vitamins A, B, and E. The oil assists with the removal of dead skin cells and impurities as well as reduces inflammation, redness and itching of skin. Sweet almond oil is a good emollient and has properties that make it very useful for treating skin problems such as psoriasis and eczema. Sweet almond oil stimulates hair growth, strengthens hair reducing hair breakage and adds shine, smoother ends and less frizz.

Lavender oil. Not only is lavender good for the mind, but it is also beneficial for a healthy scalp and hair growth. Because lavender oil is a natural anti-inflammatory, it is helpful for maintaining a healthy scalp and can be used to treat dandruff and psoriasis of the scalp. By keeping these scalp conditions at bay, and enhancing the blood circulation of the scalp, the scalp is rejuvenated and shows signs of improved health. Additionally, Lavender oil enhances blood circulation, to further improve the health of the scalp.

Olive oil. One of the more surprising benefits of olive oil is that it can prevent and even cure hair loss. When people lose hair, it is due to a hormone responsible for the shrinkage of the hair follicle shaft. However, the production of that hormone, called DHT (dihydrotestosterone), is hampered when olive oil is applied to the scalp. The overall health of the scalp also benefits from olive oil and a healthy scalp equates to healthy hair. Additionally, the natural conditioner properties of olive oil add moisture to the scalp, an area that people tend to neglect. Besides healing a dry scalp; olive oil makes hair soft and shiny and has antibacterial and antifungal properties that fight off common scalp and hair problems. Furthermore, the application of Olive oil to the scalp can prevent or hamper dandrugg or even head lice.

Grape seed oil. Grape seed oil helps hair to grow faster, and the essential oil contains almost all the important nutrients for hair to grow healthily. It has vitamin E, linoleic acid, proteins and minerals that nourish the hair and scalp almost instantly after the oil is topically applied. In general, hair grows faster and stronger when it is provided with a nourishing supply of vitamin E and other important nutrients. Additionally, Grape seed oil has several important health benefits in that it is a good source of essential fatty acids and vitamin E, also the polyphenols and flavonoids found in the oil contain strong antioxidant compounds. Furthermore, the flavonoid 'oligomeric procyanidin', found in grape seed oil is an incredibly strong antioxidant, about 50 times stronger than antioxidants such as vitamin C and E which allows grape seed oil containing this flavonoid to be a very strong free radical scavenger and provide protection against cellular and tissue damage caused by free radicals. Additionally, Grape seed oil can help strengthen and repair damaged or broken capillaries and blood vessels.

Carrot oil. Carrot oil is an effective hair and a skincare emulsion because it is rich in carotene, antioxidants and amino acids. Carrot oil is great for skin renewal as well as hair growth. It also revitalizes and tones the skin, helping in cases of dermatitis, eczema and rashes. Since carrot seed oil contains carotene and vitamin A, it is also very good for healthy skin and hair.

*Arnica* oil. *Arnica* oil helps speed the healing process of hair and tissues by moving waste-bound fluids out and moving cleansing fluids and platelets into an affected area. *Arnica* oil is considered as one of the best ethereal oils to prevent hair loss and it is a trusted herbal cure for alopecia neurotic. *Arnica* oil based preparations are also well known in homeopathy as a cure for various hair related problems such as diffuse alopecia, graying hair and dandruff. Additionally, *Arnica* oil is a strong anti-inflammatory agent with antioxidant properties that enrich the scalp and protect hair from damage caused by harsh elements and environmental pollution.

Tea Tree Oil. Tea Tree oil helps to remove dead skin cells and is a powerful scalp purifier. The oil may be used to treat scalp conditions such as psoriasis and dandruff and promotes hair growth by improving blood circulation all over the scalp. Tea tree oil encourages seating which, in turn, leads to detoxification of the skin as pollutants and a lot of infectious agents are flushed out of the body.

Pseudocollagen. Pseudocollagen (Yeast-derived collagen equivalent): This yeast-derived, dermal-matrix material is a true moisturizing glycoprotein taken from living cells. It is extracted from yeast by a controlled process which preserves its high molecular weight and native structure, making it the perfect addition to skin and hair products. Pseudocollagen can be used in a wide variety of hair-care formulas, providing body and shine, and leaving permed hair with a softer, less raspy look.

*Eucalyptus* Oil. *Eucalyptus* oil increases the elasticity of hair making it stronger and more resistant to hair breakage and split ends. The oil has antiseptic and antifungal properties, and can keep the scalp healthy by preventing microbial growth. Which, in turn can promote healthy growth of hair. This oil is effective at getting rid of dandruff, which is a common scalp problem that can cause hair loss. Dandruff can also inhibit the growth of hair. *Eucalyptus* oil can provide relief in other scalp problems, such as mild forms of psoriasis, scalp pimples, and dry scalp. Additionally, the oil can moisturize and soothe dry skin and improve blood flow to the scalp, which can help eliminate the build up of oil and bacteria in the hair follicles. Because proper blood circulation ensures the supply of adequate nutrients to the hair follicles, which stimulates hair growth, by improving scalp circulation this oil can revitalize dull hair and improve hair texture. *Eucalyptus* oil also increases the production of ceramide, a type of lipid molecule that naturally occurs in hair strands. Ceramides help keep the hair cuticle intact, and prevent the loss of natural moisture and protein from hair strands. This in turn increases the strength, shine, and elasticity of hair.

Cedarwood oil. Cedarwood essential oil has powerful antiseptic, anti-seborrheic, astringent and fungicidal properties which makes it an effective cure and prevention agent for fungal infections of the scalp and irritating dandruff conditions. The astringent properties of the oil help deep cleanse the scalp and hair shaft to allow the roots and follicles to breathe, whereas the anti-seborrheic properties correct imbalanced functioning of the sebaceous glands by arresting excess sebum production.

Avocado oil. Avocado oil is full of healthy hair vitamins that promote and maintain silky locks of hair. The oil also contains amino acids that help bind split ends, nourish hair follicles and promote faster hair growth. The various nutrients in avocado oil protect hair from environmental pollution. Additionally the oil can strengthen hair strands, add a dash of shine and make hair super soft.

Jojoba oil. Jojoba oil has antibacterial and fungicidal properties, that can be used for keeping the scalp healthy. The oil aids in reducing hair loss, caused by factors like scalp dermatitis, psoriasis, and eczema. Jojoba oil is an excellent hair conditioner, which can be used to get rid of dry, frizzy, and unmanageable hair. Additionally, the oil helps seal the moisture in the hair shaft, and adds a natural glow and luster to hair by minimizing the damage caused by harsh chemicals and pollutants.

Shea Butter. The main components of shea butter include oleic acid, stearic acid, linoleic acid and others. The butter is absorbed quickly into the skin as it melts at body temperature. Shea butter is known for its healing properties, which can be attributed to the presence of several fatty acids and plant sterols such as oleic, palmitic, stearic and linolenic acids. These oil-soluble components do not undergo saponification or convert into soap upon coming into contact with alkali. Additionally, Shea butter is more non-saponifiable than other nut oils and fats, thus imparting it a great healing potential for the skin. The butter contains plant antioxidants such as vitamins A and E, as well as catechins. The vitamins A and E protect the cells from free radicals and environmental damage. Furthermore Shea butter has cinnamic acid esters in the shea fat which help in preventing skin damage from ultraviolet radiation. Several derivatives of cinnamic acid are found in shea butter which exhibit anti-inflammatory properties. Being rich in precious constituents such as unsaturated fats with a large proportion of non-saponifiable components, essential fatty acids, vitamins E and D, phytosterols, provitamin A and allantoin, shea butter is considered a super food for the skin.

*Aloe Vera* oil. *Aloe Vera* oil provides a great benefit for hair loss prevention as well as removing dandruff and treating seborrhea. When dandruff occurs there is usually an accompanying hair loss problem. In fact, in order to properly treat hair loss one needs to first handle the dandruff problem. The natural pH level of hair and scalp is between 4 and 4.5, while aloe vera's pH level is 4.5 to 5.5. Therefore, the plant can be used to restore hair and scalp to its natural condition without using additional chemical substances. A proper pH level of the hair and scalp helps the hair maintain its ability to retain moisture.

Sage oil. Sage oil is among the best scalp purifiers. A strong infusion of Sage essential oil used as a rinse is believed to darken gray hair and is among the most trusted herbal loss solutions. Additionally, Sage oil is loaded with antioxidant, antiseptic and antifungal properties.

Polyglyceryl Oleate. Polyglyceryl Oleate is a distilled triyglycerol ester based on vegetable oleic acid, that is PEG-free. It is a yellow to amber liquid in color and has a bland odor. Polyglyceryl Oleate disperses in water and has a hydrophilic-lipophilic balance (HLB) of 5 (gives water-in-oil emulsions). The INCI Name is Polyglyceryl-4oleate. The general chemical properties of Polyglyceryl Oleate make it an excellent emulsifier (which freely enables water & oil to mix).

PEG-7 Glyceryl Cocoate. Description: Non-ionic, ethoxylated polyethylene glycol ester made from glycerin & coconut oil. It is a clear oily liquid, with a characteristic odor. The compound is soluble in water & alcohols, but insoluble in oils. The HLB value is 11 (gives oil-in-water emulsions). The CAS# is 68201-46-7 and the INCI Name is: Polyoxyethylene (PEG-7) glyceryl monococoate. The compound properties are that it is a Multifunctional agent with excellent emulsifying, emollient, refatting & thickening properties, and is useful as a surfactant & foam booster, and has good conditioning effects for soft & smooth skin.

By formulated combinations of the above ingredients listed above in a single formulation the end result is a powerhouse formulation with the ability to stop and prevent hair loss, fast and effectively. The combination of the selected ingredients work together to straighten, clarify, neutralize and heal the scalp. The embodied formulations are a medicine for hair and scalp. They heal from the root to the ends of the hair. The embodied formulations are able to penetrate deep in to the layers of skin. And have the ability to clarify the hair follicle from impurities and unclog the follicle. By unclogging the hair follicle, the formulation allows the hair to grow and expand without any restrictions. Thus creating the ideal environment for re-growth of healthy hair. Embodied formulations are also able to rebuild the damaged tissue over a short amount of time making it ideal for those with chemically damaged scalps to regenerate the ability to produce healthy hair. Additionally, the embodied formulations assist those with skin issues, calms dermatitis, eczema and other skin related issues. Each ingredient is unique in their own way, however when combined together at a proper ratio there is a synergy of components that allows the formulation to have a noticeable effect after the first use.

Details of the present invention will now be discussed by reference to the following non-limiting examples.

TABLE 1

Example Formulation 1

| Ingredients | Oz | Total % | Range |
| --- | --- | --- | --- |
| Rose water | 54 | 28.8% | 25-30% |
| *Eucalyptus* oil | 14 | 7.5% | 5-10% |
| Castor oil | 12 | 6.4% | 5-8% |
| Thyme oil | 12 | 6.4% | 5-8% |
| Rosemary Oil | 10 | 5.3% | 4-6% |
| German Chamomile oil | 08 | 4.3% | 3-5% |
| Carrot Oil | 08 | 4.3% | 3-5% |
| Coconut oil | 06 | 3.2% | 2-4% |
| Sweet almond oil | 06 | 3.2% | 2-4% |
| Cedenvood oil | 04 | 2.1% | 1-3% |
| Olive oil | 04 | 2.1% | 1-3% |
| Grape seed oil | 04 | 2.1% | 1-31-3% |
| Lavender oil | 04 | 2.1% | .5-2.5% |
| *Arnica* oil | 03 | 1.6% | .5-2.5% |
| Jojoba oil | 03 | 1.6% | .5-2.0% |
| *Aloe Vera* oil | 02 | 1.1% | .5-2.0% |
| Tea tree oil | 02 | 1.1% | .5-2.0% |
| Pseudocollogen | 02 | 1.1% | .5-2.0% |
| Vegetable glycerin | 02 | 1.1% | .5-2.0% |
| Shea Butter | 02 | 1.1% | .5-2.0% |
| Sage oil | 0.5 | 0.3% | 0.1-0.6% |
| Polyglyceryl Oleate | 20 | 10.7% | 8-12% |
| PEG-7-Glyceryl Cocoate | 5 | 2.7% | 2-4% |
| Total Oz | 187.5 | | |

Methods of Formulating the product. The methods of formulating utilize two containers, a first container has the oils and other ingredients and the second container has the rose water and the emulsifiers. The exemplary formulation batch shown includes a final batch amount of about 187.5 ounces.

Step 1—In a first container the following ingredients are mixed together in the following amounts: 14 Oz of *Eucalyptus* oil, 12 Oz of Castor oil, 12 Oz of Thyme oil, 10 Oz of Rosemary oil, 8 oz of German Chamomile oil, 8 Oz if Carrot oil, 6 Oz of Coconut oil (melted in a pot before adding), 6 Oz of Sweet almond oil, 4 Oz of Cederwood oil, 4 Oz of Olive oil, 4 Oz of Grape seed oil, 4 Oz of Lavender oil, 3 Oz of *Arnica* oil, 3 Oz of Jojoba oil, 2 Oz of *Aloe Vera* oil, 2 oz of Tea tree oil, 2 Oz of Pseudocollagen, 2 Oz of Vegetable glycerin, 2 oz of Shea Butter (Melted in a pot before adding), 0.5 Oz of Sage oil.

Step 2—In a second container the following ingredients are mixed together in the following amounts: 54 Oz of Rose water, 20 Oz of Polyglyceryl Oleate, and 5 Oz of PEG-7-Glyceryl Cocoate.

Step 3—After step 1 and 2 are complete the ingredients from the first container are slowly stirred into the second container ingredients and mixed. After mixing the ingredients together the formulation comprises a creamy serum that is ready to be used.

In other exemplary embodiments, the formulation may be changed and various other ingredients may be added to change some of the characteristics of the formulation to create gels, mousses, shampoos, conditioners, rinses and the like. The application of these products may vary depending upon whether the user is trying to prevent the loss of hair or trying to grow hair.

For instance, in yet another embodiment of the present disclosure, the formulation for treatment of hair loss comprise the following ingredients/elements instead: *Rosa Centifolia* Flower Water, Polyglyceryl-6 Distearate, Polyglyceryl-3 Diisostearate, *Thymus Vulgaris* (Thyme) Oil, *Eucalyptus Globulus* Leaf Oil, *Ocimum Basilicum* Hairy Root Culture Extract, *Helianthus Annuus* (Sunflower) Seed Oil, *Ricinus Communis* (Castor) Seed Oil, Jojoba Esters, *Arnica Montana*, Cetyl Alcohol, Glyceryl Stearate, *Cocos Nucifera* (Coconut) Oil, Ceteth-20, Steareth-20, Glycerin, *Acacia Decurrens* Flower Wax, *Helianthus Annuus* (Sunflower) Seed Wax, Polyglycerin-3, *Pisum Sativum* (Pea) Sprout Extract (Pea) Sprout Extract, Biotin, *Daucus Carota Sativa* (Carrot) Seed Oil, *Simmondsia Chinensis* (Jojoba) Seed Oil, *Butyrospermum Parkii* (Shea Butter), *Olea Europaea* (Olive) Oil, Algae Extract, Butylene Glycol, *Prunus Amygdalus Dulcis* (Sweet Almond) Oil, *Lavandula Angustifolia* (Lavender) Oil, *Melaleuca Alternifolia* (Tea Tree) Leaf Oil, Xanthan Gum, *Vitis Vinifera* (Grape) Seed Oil, *Juniperus Mexicana* Wood Oil, *Salvia Officinalis* (Sage) Oil, German Blue (*Matricaria Chamomilla*) Oil, Phenethyl Alcohol, Glycerine, *Citrus Reticulata* Fruit Extract, *Citrus Aurantium Amara* Fruit Extract, *Citrus Sinensis* Peel Extract, Ascorbic acid, Citric acid and/or Lactic acid.

Details of the formulation above will be discussed by reference to the following non-limiting examples.

TABLE 2

Example Formulation 2

| Ingredients | Percentage | Unit | Amount |
| --- | --- | --- | --- |
| Rose Water | 45% | Oz | 2.25 |
| *Eucalyptus* oil | 4.80% | Oz | 0.24 |
| Castor Oil | 3% | Oz | 0.15 |
| Thyme Oil | 5% | Oz | 0.25 |

TABLE 2-continued

Example Formulation 2

| Ingredients | Percentage | Unit | Amount |
|---|---|---|---|
| Blue Chamomile Oil | 0.14% | Oz | 0.007 |
| Carrot Seed Oil | 1.50% | Oz | 0.075 |
| Coconut Oil | 1% | Oz | 0.05 |
| Almond Oil | 1% | Oz | 0.05 |
| cederwood | 0.50% | Oz | 0.025 |
| Olive oil | 1% | Oz | 0.05 |
| grape seed oil | 0.50% | Oz | 0.025 |
| Lavender oil | 1% | Oz | 0.05 |
| *Arnica* oil | 2% | Oz | 0.1 |
| jojoba oil | 1% | Oz | 0.05 |
| Tea tree | 0.50% | Oz | 0.025 |
| Pseudocollogen | 1% | Oz | 0.05 |
| Glycerin | 2.50% | Oz | 0.125 |
| Shea Butter | 1.39% | Oz | 0.07 |
| Sage oil | 0.17% | Oz | 0.009 |
| AnaGain ® | 2% | Oz | 0.1 |
| RootBio TEC HO | 2% | Oz | 0.1 |
| Biotin | 0.50% | Oz | 0.025 |
| Sharon BioMix Free 1 | 1% | Oz | 0.05 |
| Tefose ® HC | 5% | Oz | 0.25 |
| Plurol ® sterarique WL1009 | 6% | Oz | 0.3 |
| Plurol ® Diisoctearique CG | 5% | Oz | 0.25 |
| Acticire ® | 5% | Oz | 0.25 |
| Keltrol ® CG | 0.50% | Oz | 0.025 |
| Total | 100% | | 5.000 Oz |

The percentage of each ingredient may be adjusted depending on the user's needs and is not limited by the formula above. For example and not by way of limitation, the percentage of each ingredient can be adjusted like the following: 30-60% Rose Water, 2-7% *Eucalyptus* oil, 1-6% Castor Oil, 2-8% Thyme Oil, 0.05-0.5% Blue Chamomile Oil, 0.5-3% Carrot Seed Oil, 0.5-3% Coconut Oil, 0.5-3% Almond Oil, 0.1-1% cederwood, 0.5-3% Olive oil, 0.1-1% grape seed oil, 0.5-3% Lavender oil, 0.5-4% *Arnica* oil, 0.5-3% jojoba oil, 0.1-1.0% Tea tree, 0.5-3% Pseudocollogen, 0.50-5% Glycerin, 0.1-4% Shea Butter, 0.01-0.40% Sage oil, 0.5-4% AnaGain®, 0.5-4% RootBio TEC HO, 0.1-1.0% Biotin, 0.5-3% Sharon BioMix Free 1, 2-8% Tefose® HC, 3-9% Plurol® sterarique WL1009, 2-8% Plurol® Diisoctearique CG and 2-8% Acticire®, 0.1-1.0% Keltrol® CG.

In this embodiment, the method of formulating the product comprises four phases A, B, C and D.

Phase A—Mix Biotin and Rose Water till dissolved. Add Keltrol® CG to the mix of Biotin and Rose Water and Mix with a High speed shear for approximately 20 minutes.

Phase B—Add the oils and active ingredients together and mix to combine.

Phase C—Add Tefose® HC, Acticire®, Plurol® Stearique WL1009, Plurol® Diisostearique CG and heat them to combine.

Phase D—Add phase B and C together and mix for approximately 5 minutes. Add phase A to Phase B and C and mix till all combined and makes a cream like mixture. At the end add Sharon Biomix free 1 and mix for approximately 5 minutes till they are all combined.

Example Formulation 3 (Silve Rose)

TABLE 3

Example Formulation 3

| Item | Raw Material Name | % (w/w) | LBS |
|---|---|---|---|
| | STEP-1 | | |
| 1 | Deionized Water | 26.429 | 385.863 |
| 2 | Rosewater | 30.000 | 438.000 |
| 3 | Natrosol 250HHR | 0.500 | 7.300 |
| 4 | Glycerin | 5.000 | 73.000 |
| | STEP-2 | | |
| 5 | Tefose HC | 3.200 | 46.720 |
| 6 | Plurol Sterarique WL-1009 | 2.500 | 36.500 |
| 7 | Plurol Diisostearicque CG | 2.000 | 29.200 |
| 8 | Acticire | 3.000 | 43.800 |
| 9 | Cetearyl alcohol | 3.000 | 43.800 |
| 10 | Grape Seed Oil | 0.500 | 7.300 |
| 11 | Jojoba Oil | 0.500 | 7.300 |
| 12 | Castor Oil | 3.000 | 43.800 |
| 13 | Olive Oil | 1.000 | 14.600 |
| 14 | Shea butter | 0.500 | 7.300 |
| 15 | Sweet Almond oil | 0.500 | 7.300 |
| 16 | Coconut Oil | 0.500 | 7.300 |
| 17 | Biotin | 0.001 | 0.015 |
| | STEP-3 | | |
| 18 | Thyme Oil | 3.500 | 51.100 |
| 19 | *Eucalytus* Oil | 3.800 | 55.480 |
| 20 | Carrot Oil | 0.200 | 2.920 |
| 21 | Lavender OIL | 0.500 | 7.300 |
| 22 | Tea Tree Oil | 0.500 | 7.300 |
| 23 | Sage Oil | 0.170 | 2.482 |
| 24 | Cedarwood Oil Texas Redistilled | 0.100 | 1.460 |
| 25 | Chamomile Oil Blue | 0.100 | 1.460 |
| | STEP-4 | | |
| 26 | *Arnica* Oil | 2.000 | 29.200 |
| 27 | Rootbio tee HO | 4.000 | 58.400 |
| 28 | Euxyl PE 9010 | 1.000 | 14.600 |
| 29 | Anagain | 2.000 | 29.200 |
| | Total Batch: | 100.000 | 1460.000 |

1 gallon water = 8.33 lbs
**Gallons: 46.32

STEP-1—charge tank with item 1 and add item 2 mix for 10 mins. Premix items 3-4 and add to batch. Begin mixing. Add Items 4-5. Heat Phase A to 70-75 C.

STEP-2—Phase B in another container add items 5-17 and begin heating 75-70 C. When Both STEP-1 and STEP-2 reached the same temperature, combine them and mix for 10 mins.

STEP-3—Start cooling to 55-50 C and add items 18-25 until incorporated in batch.

STEP-4—Further Cool and add items 26-29. Mix well and homogeneous.

The percentage of each ingredient listed in Table 3 may be adjusted depending on the user's needs and is not limited by the formula above. For example and not by way of limitation, the percentage of each ingredient can be adjusted like the following: 20-30% Deionized Water; 20-40% Rosewater; 0.1-1.0% Natrosol 250HHR; 2-8% Glycerin; 1-5% Tefose HC; 1-5% Plurol Sterarique WL-1009; 1-5% Plurol Diisostearicque CG; 1-5% Acticire; 1-5% Cetearyl alcohol; 0.1-1.0% Grape Seed Oil; 0.1-1.0% Jojoba Oil; 1-5% Castor Oil; 0.1-2.0% Olive Oil; 0.1-1.0% Shea butter; 0.1-1.0% Sweet Almond oil; 0.1-1.0% Coconut Oil; 0.0001-0.002% Biotin; 1-5% Thyme Oil; 1-5% *Eucalyptus* Oil; 0.1-1.0%

Carrot Oil; 0.1-1.0% Lavander Oil; 0.1-1.0% Tea Tree Oil; 0.01-0.5% Sage Oil; 0.01-0.5% Cedarwood Oil Texas Redistilled; 0.01-0.5% Chamomile Oil Blue; 1-5% *Arnica* Oil; 1-5% Rootbio tec HO; 0.1-2% Euxyl PE 9010; and 1-5% Anagain.

Natrosol™ 250 HR/HHR Hydroxyethylcellulose, PC Grade is a nonionic water-soluble polymer. This white, free-flowing granular powder can be used in a variety of applications, including hair conditioner, liquid soaps, shave gels and foams, toothpaste (high salt), wipes (baby and adult), makeup/mascara, AP/Deodorant solids, and lubricant gels. Solutions of Natrosol HEC are pseudoplastic or shear-thinning. As a result, personal care products formulated with Natrosol HEC dispense rich and thick from the container, but spread easily on hair and skin.

Rose water is a flavoured water made by steeping rose petals in water. It is the hydrosol portion of the distillate of rose petals, a by-product (co-product) of the production of rose oil for use in perfume. It is used to flavour food, as a component in some cosmetic and medical preparations, and for religious purposes throughout Europe and Asia.

Plurol® Stearique WL 1009 is a natural, PEG-free, O/W sensory emulsifier, bringing a distinct soft and powdery feel to cosmetic formulations. The gentleness of this emulsifier makes it ideal for sensitive skin and baby care lines. It is certified natural by ECOCERT/COSMOS and NPA.

Plurol® Diisostearique CG is a natural, PEG-free, W/O sensory emulsifier, bringing a distinct soft and powdery feel to cosmetic formulations. The gentleness of this emulsifier makes it ideal for sensitive skin and baby care lines, while its staying power makes it ideal also for water resistance and long-wear color cosmetics. It may be used cold process, and is certified natural by ECOCERT/COSMOS and NPA.

Acticire® is a natural, multifunctional active texture agent based on Jojoba, Mimosa, and Sunflower waxes. In skin care, Acticire® acts as an emollient, bringing softness to the skin, and as an active, repairing, protecting, and moisturizing dry, damaged skin. Acticire® also brings thickening, richness, and luxury to skin care formulations. In lipsticks and anhydrous balms, Acticire® has the unique ability to enable the inclusion of water or water soluble actives, while maintaining a stable formulation. Substantiated in vivo. Preservative free.

RootBioTec HO is a potent basil hairy root extract that has been designed for users to regain fuller and denser hair. The product is based on a unique, sustainable technology for cosmetic actives—the so-called "hairy roots" technology. RootBioTec HO successfully reduces hair loss by inhibiting 5α reductase II activity and through stimulating the dermal papilla cells in hair follicles.

Euxyl® PE 9010 is a liquid cosmetic preservative based on phenoxyethanol and ethylhexylglycerin. The addition of ethylhexylglycerin affects the interfacial tension at the cell membrane of microorganisms, improving the preservative activity of phenoxyethanol. Euxyl® PE 9010 has a broad, balanced spectrum of effect against bacteria, yeasts and mould fungi.

Oil/water and water/oil systems as well as shampoos and bath additives preserved with use concentrations of between 0.5 and 1.0% Euxyl® PE 9010 proved are well preserved even after three months storage at +40° C. Euxyl® PE 9010 is used as a preservative for cosmetics and toiletries. The product is used at a recommended use concentration of 0.5-1.0%. In accordance with the conditions stipulated in Directive 76/768/EEC Euxyl® PE 9010 may be used in cosmetic preparations (leave-on and rinse-off) in a use concentration up to a maximum of 1.1%.

AnaGain™ is used for stimulating hair growth and fighting hair loss. Based on sprouts of organic pea, AnaGain™ reduces hair loss by inducing dermal papilla cells to reactivate hair growth. AnaGain™ was shown, thanks to DNA microarray analysis of plucked hair follicles, to activate, in the dermal papilla, specific signal molecules which are required to initiate the growth of a new hair. By reactivating hair growth, AnaGain™ helps the hairs to keep their original density and thickness. Applications include anti-hair loss and hair-regrowth formulations, anti-aging hair care products, and can be used in tonics, serums, conditioners, masks, and shampoos.

Hair loss prevention and restoration solution of the present disclosure is designed with all organic and natural ingredients for users to regain fuller and denser hair. With its unique blend of all organic and natural active ingredients, the disclosed solution is able to perform on multiple levels in preventing hair loss with minimal to no side effect. Formula provides health-promoting phytonutrients, potent antioxidants, and provitamins. It is also enriched with moisturizing, nourishing, anti-aging, detoxifying, anti-inflammatory, anti-viral, and anti-microbial properties.

Figure 2:
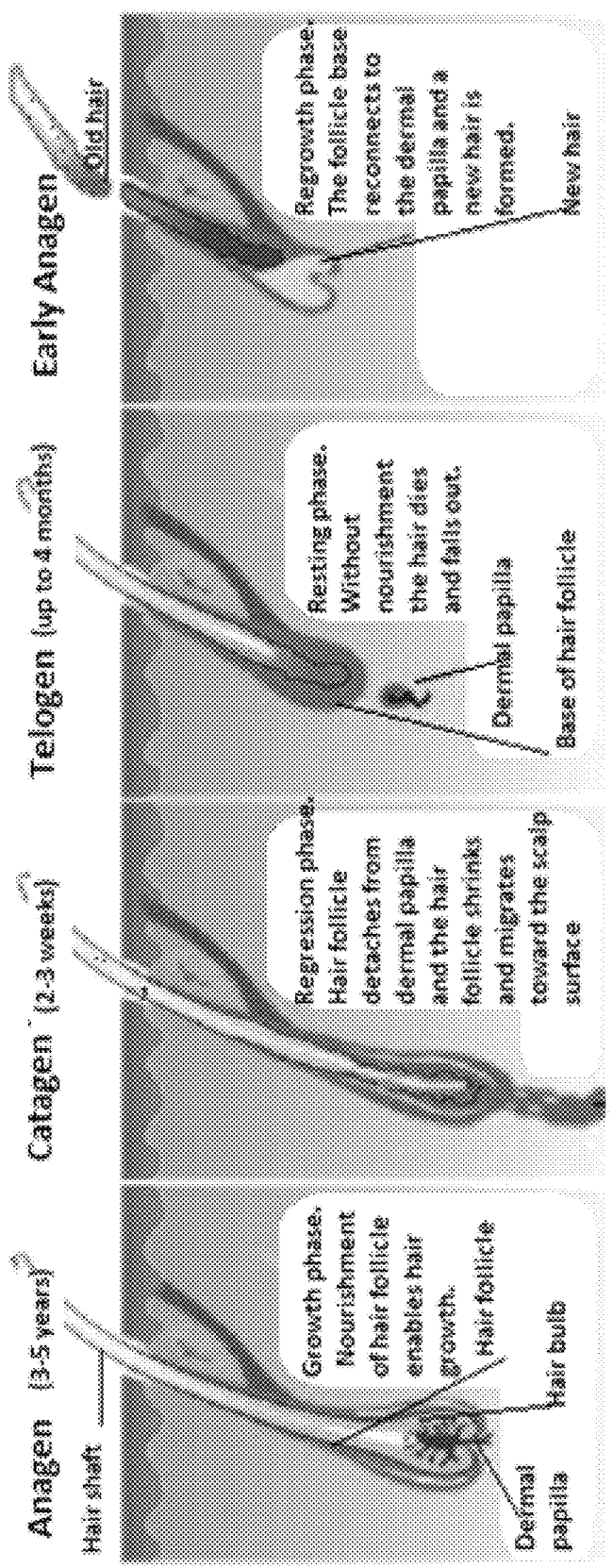
FIG. 2 demonstrates an illustration of hair growth cycle.

As shown by FIG. 2, imbalance of the hair growth cycle occurs when too many hairs remain in a resting stage. Each hair follicle undergoes an independent growth cycle and originates from hair matrix cell. Each hair undergoes three stages of hair growth: The first stage is anagen, followed by catagen, and ending with the resting period telogen. Telogen is where the hair follicle returns to the anagen phase, and a new strand of hair begins to form.

The formula of the present disclosure is able to penetrate deep into the hair bulb where the hair matrix embeds the dermal papilla. Our formula produces specific signaling molecules in order to initiate growth of new hair. It stimulates the dermal papilla, successfully resumes hair growth from the resting stage, telogen, and as a result increases proliferation of the dermal papilla cells in the hair follicle.

Figure 3:
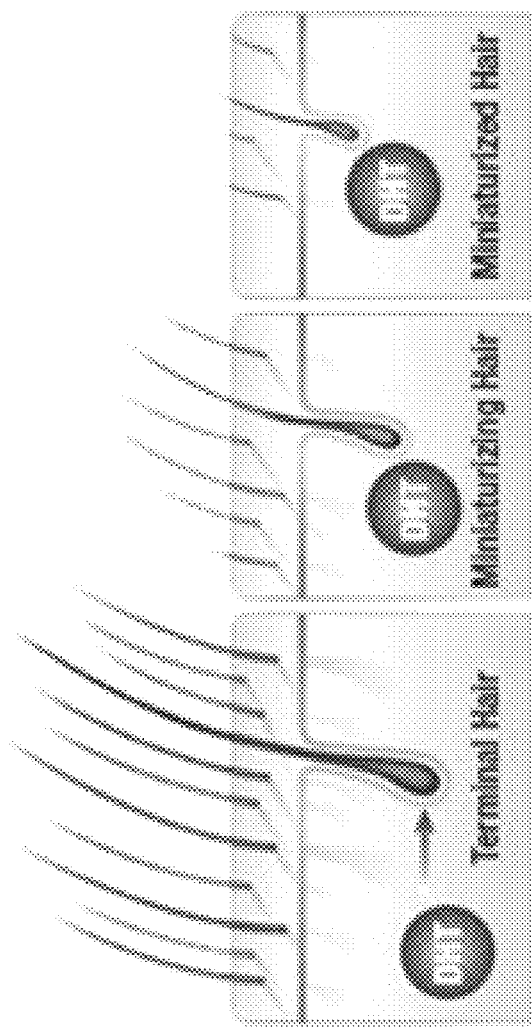
FIG. 3 demonstrates an illustration of DHT formation.

As shown by FIG. 3, DHT (dihydrotestosterone) formation is caused by an enzyme called 5-alpha-reductase which converts testosterone to dihydrotestosterone, the hair loss inducing hormone. When formed, DHT binds itself to the hair follicle and causes it to miniaturize. When DHT binds to androgen of the hair follicle, the hair follicle starts to shrink and becomes less visible. The miniaturization of the hair follicles can progress until the hair resembles "peach fuzz." Due to its unique formula, the disclosed formula is also able to reduce hair loss and miniaturization of the hair by inhibiting DHT (dihydrotestosterone) formation, promoting detoxification of the scalp, micro blood circulation, follicle stimulation, and by creating a favorable environment for re-growth. The disclosed formula effectively targets the hair dermal papilla and is able to reduce hair loss in men and women providing healthier looking scalp and hair.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In other exemplary embodiments, the formulation may be changed and various other ingredients may be added to change some of the characteristics of the formulation to create gels, mousses, shampoos, conditioners, rinses and the like. The application of these products may vary depending upon whether the user is trying to prevent the loss of hair or trying to grow hair. Additionally, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A formulation of a cream for use in the treatment of hair loss comprising:
   20-30% Deionized Water;
   20-40°% Rosewater;
   1-5% Cetearyl alcohol;
   0.0001-0.002% Biotin;
   0.1-1.0% hydroxyethylcellulose; and
   2-8% Glycerin.

2. The formulation of claim 1 further comprising:
   1-5% Cetyl Alcohol (and) Glyceryl Stearate (and) Ceteth-20 (and) Steareth-20;
   1-5% Polyglyceryl-6 Distearate;
   1-5% Polyglyceryl-3 Diisostearate;
   1-5% Jojoba Esters (and) Helianthus Annuus Seed Wax (and) Acacia Decurrens Flower Wax (and) Polyglycerin-3;
   0.1-1.0%/o Grape Seed Oil;
   0.1-1.0% Jojoba Oil;
   1-5% Castor Oil;
   0.1-2.0% Olive Oil;
   0.1-1.0% Shea butter;
   0.1-1.0% Sweet Almond oil; and
   0.1-1.0% Coconut Oil.

3. The formulation of claim 1 further comprising:
   1-5% Thyme Oil;
   1-5% Eucalytus Oil;
   0.1-1.0% Carrot Oil;
   0.1-1.0% Lavender Oil;
   0.1-1.0% Tea Tree Oil;
   0.01-0.5% Sage Oil;
   0.01-0.5% Cedarwood Oil Texas Redistilled; and
   0.01-0.5% Chamomile Oil Blue.

4. The formulation of claim 1 further comprising:
   1-5% Arnica Oil;
   1-5% Ocimum Basilicum Hairy Root Culture Extract (and) Helianthus Annuus Seed Oil (and) Cocos Nucifera Oil;
   0.1-2% Phenoxyethanol (and) Ethylhexylglycerin; and
   1-5% Pisum Sativum Sprout Extract.

5. A formulation of a cream for use in the treatment of hair loss comprising:
   20-30% Deionized Water;
   20-40% Rosewater;
   0.1-1.0% hydroxyethylcellulose;
   2-8% Glycerin;
   1-5% Cetyl Alcohol (and) Glyceryl Stearate (and) Ceteth-20 (and) Steareth-20;
   1-5% Polyglyceryl-6 Distearate;
   1-5% Polyglyceryl-3 Diisostearate;
   1-5% Jojoba Esters (and) Helianthus Annuus Seed Wax (and) Acacia Decurrens Flower Wax (and) Polyglycerin-3;
   1-5% Cetearyl alcohol;
   0.1-1.00% Grape Seed Oil;
   0.1-1.0% Jojoba Oil;
   1-5% Castor Oil;
   0.1-2.0% Olive Oil;
   0.1-1.0% Shea butter;
   0.1-1.0% Sweet Almond oil;
   0.1-1.0% Coconut Oil; and
   0.0001-0.002,% Biotin.

6. The formulation of claim 5 further comprising:
   1-5% Thyme Oil;
   1-5% Eucalytus Oil;
   0.1-1.0% Carrot Oil;
   0.1-1.0% Lavender Oil;
   0.1-1.0% Tea Tree Oil;
   0.01-0.5% Sage Oil;
   0.01-0.5% Cedarwood Oil Texas Redistilled; and
   0.01-0.5% Chamomile Oil Blue.

7. The formula tion of claim 5 further comprising:
   1-5% Arnica Oil;
   1-5% Ocimum Basilicum Hairy Root Culture Extract (and) Helianthus Annuus Seed Oil (and) Cocos Nucifera Oil;
   0.1-2% Phenoxyethanol (and) Ethylhexylglycerin; and
   1-5% Pisum Sativum Sprout Extract.

8. A formulation of a cream for use in the treatment of hair loss comprising:
   30-60% Rose Water;
   2-7% Eucalyptus oil;
   1-6% Castor Oil;
   2-8% Thyme Oil;
   0.05-0.5% Blue Chamomile Oil;
   0.5-3% Carrot Seed Oil;
   0.5-3% Coconut Oil;
   0.5-3% Almond Oil;
   0.1-1% cederwood;
   0.5-3% Olive oil;
   0.1-1% grape seed oil;
   0.5-3% Lavender oil;
   0.5-4% Arnica oil;
   0.5-3% jojoba oil;
   0.1-1.0% Tea tree;
   0.5-3% Pseudocollagen;
   0.50-5% Glycerin;
   0.1-4% Shea Butter;
   0.01-0.40% Sage oil;
   0.1-1.0% Biotin.

* * * * *